United States Patent [19]

Mattson

[11] Patent Number: 5,228,070
[45] Date of Patent: Jul. 13, 1993

[54] CONSTANT IMAGE QUALITY CT SCANNER WITH VARIABLE RADIATION FLUX DENSITY

[75] Inventor: Rodney A. Mattson, Mentor, Ohio

[73] Assignee: Picker International, Inc., Highland Hts., Ohio

[21] Appl. No.: 856,621

[22] Filed: Mar. 24, 1992

Related U.S. Application Data

[63] Continuation-in-part of Ser. No. 577,685, Sep. 4, 1990, Pat. No. 5,166,961, which is a continuation-in-part of Ser. No. 260,403, Oct. 20, 1988, Pat. No. 4,965,726.

[51] Int. Cl.$^5$ .............................................. G21K 5/10
[52] U.S. Cl. ........................................ 378/19; 378/4; 378/95; 378/146; 378/108
[58] Field of Search ..................... 378/4, 19, 15, 110, 378/112, 96, 95, 146, 108

[56] References Cited

U.S. PATENT DOCUMENTS

| | | | |
|---|---|---|---|
| 3,973,128 | 8/1976 | LeMay | 378/21 |
| 4,187,430 | 2/1980 | Schmidt | 378/99 |
| 4,193,001 | 3/1980 | Liebetruth et al. | 378/99 |
| 4,200,800 | 4/1980 | Swift | 378/10 |
| 4,547,893 | 10/1985 | Gordon | 378/19 |
| 4,672,650 | 6/1987 | Masanobu | 378/99 |
| 4,752,879 | 6/1988 | Brunnett | 378/901 |
| 4,947,412 | 8/1990 | Mattson | 378/19 |

FOREIGN PATENT DOCUMENTS 0139375  2/1985  European Pat. Off. .

Primary Examiner—David P. Porta
Assistant Examiner—Don Wong
Attorney, Agent, or Firm—Fay, Sharpe, Beall, Fagan, Minnich & McKee

[57] ABSTRACT

An x-ray source (20) rotates about a fixed cylinder (16) within which a subject of non-uniform cross-section is received. Radiation from the x-ray source passes through the subject and impinges on an arc of radiation detectors (28). Because the subject is of non-uniform cross-section, the average x-ray energy fluence impinging on the detectors across the arc varies with the relative angular position of the x-ray source and the subject. In one embodiment, a motor (18) which rotates the x-ray tube relative to the subject is controlled by a digital motor control (50). The digital motor control varies the rotational speed to a preselected angular velocity indicated by a look-up table (52) at each of a multiplicity of angular positions around the subject. The angular velocity is slowed when radiation is passing through thicker portions of the subject and accelerated when passing through thinner portions of the subject such that the average x-ray energy fluence received by the radiation detectors is substantially constant regardless of the angular position of the x-ray source. In another embodiment, an x-ray tube control circuit (82) alters the tube current such that the average x-ray energy fluence received by the detectors becomes angular position independent. In this manner, the signal-to-noise ratio at each angular position is the same and structural noise is eliminated in the resultant reconstructed image.

20 Claims, 1 Drawing Sheet

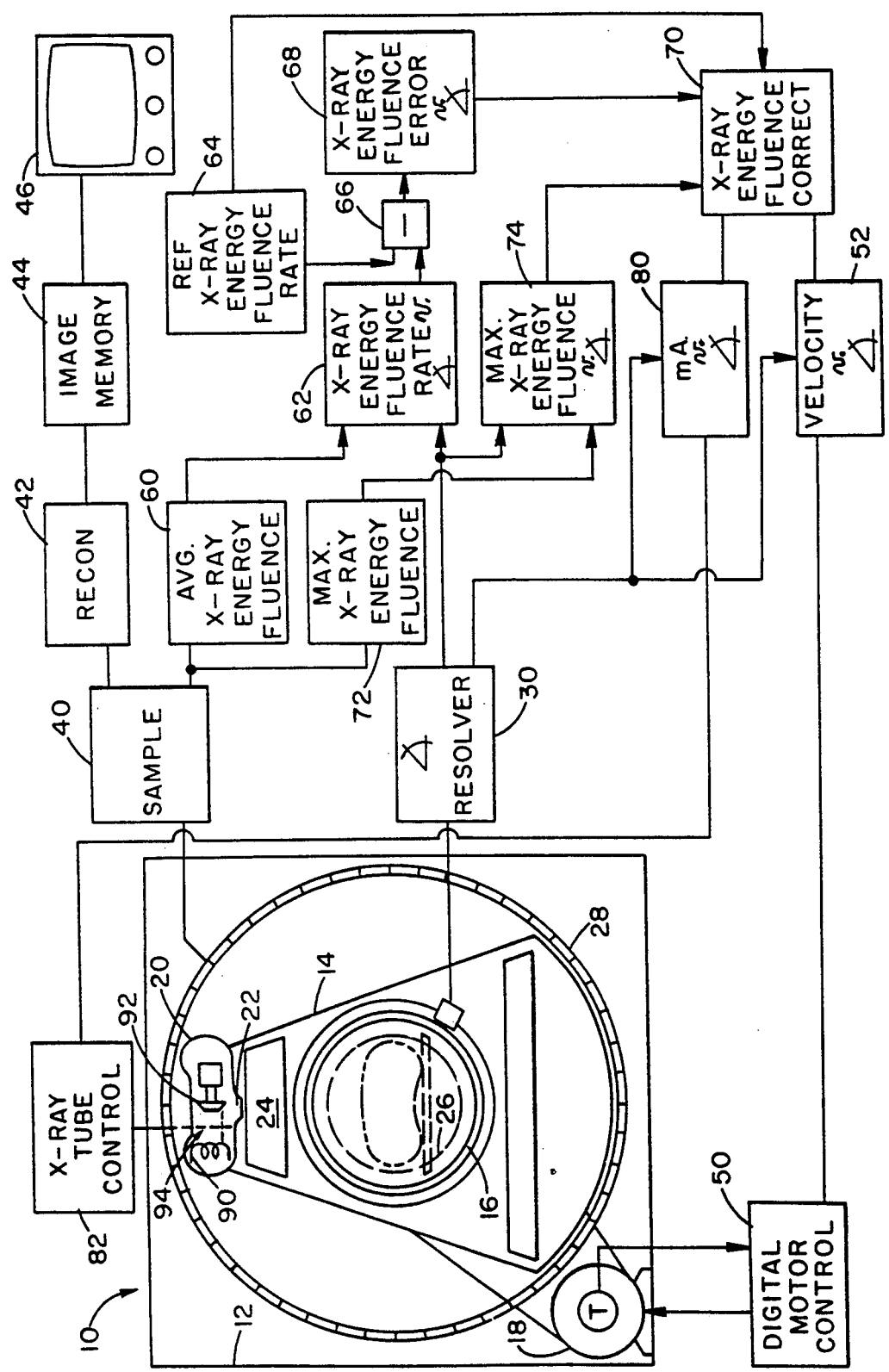

CONSTANT IMAGE QUALITY CT SCANNER WITH VARIABLE RADIATION FLUX DENSITY

This application is a continuation-in-part of application Ser. No. 07/577,685, now U.S. Pat. No. 5,166,961 filed Sep. 4, 1990 which, in turn, is a continuation-in-part of application Ser. No. 260,403 filed Oct. 20, 1988, now U.S. Pat. No. 4,965,726, issued Oct. 23, 1990.

BACKGROUND OF THE INVENTION

The present invention relates to the art of diagnostic imaging. It finds particular application in conjunction with CT scanners for medical diagnostic purposes. However, it is to be appreciated that the invention will also find application in other operations in which an object is examined from multiple directions by an x-ray source.

Conventional CT scanners have an x-ray tube which is rotated around a patient disposed in a scan circle or examination region. Radiation detectors disposed opposite the scan circle from the radiation source convert the intensity of received radiation into corresponding electrical signals. In this manner, a measure of the radiation attenuation through the patient along each of a large multiplicity of known paths is determined. From this path and attenuation data, an image is reconstructed using conventional algorithms.

The prior art CT scanners included x-ray tubes and x-ray tube control circuits designed to have a constant, unwavering radiation output. To the detector receiving the radiation, variations in x-ray tube output appeared as variations in radiation attenuation in the subject. Frequently, a reference detector was provided to monitor for any fluctuations in radiation from the x-ray tube.

Commonly, the radiation detectors integrated the amount of received radiation between samplings. In many scanners, the sampling was triggered by the angular position of the x-ray source relative to the patient. Thus, any variation in the rotational speed of the x-ray source would cause a change in the amount of time between samplings, hence the amount of radiation integrated by the detectors. Again, this rotational speed error variation in the amount of received radiation appeared as variations in the radiation attenuation properties of the subject along the corresponding path and caused errors in the resultant image. Accordingly, the prior art CT scanners were commonly designed to optimize the uniformity of the x-ray tube rotation velocity.

One of the problems in this prior art CT scanning process is that the algorithms assumed that the examined subject was generally circular in cross-section with substantially the same radiation absorptive properties in all directions. In practice however, the human body is more often irregularly elliptical than circular. Along certain paths, such as the major axis of the ellipse, there is generally substantially more radiation attenuation than along the minor axis. Because great care was taken to send the same amount of radiation along each path, the amount of radiation leaving the patient along the minor axis was much higher than the amount of radiation leaving the patient along the major axis. Commonly, the amount of radiation output by the x-ray tube was selected such that the range of radiation variation detected along the minor axis was in the upper part of the dynamic range of the detectors and variations in the range of radiation detected along the major axis was at the lower end of the dynamic range of the radiation detectors.

Because less radiation was detected along the major axis, the amplitude of the radiation relative to the noise was lower. Along the minor axis, the amplitude or amount of the received radiation was much higher relative to the background noise. That is, the noise statistics along the major axis were much greater than the noise statistics along the minor axis. This caused the resultant image to have higher noise statistics along the major axis than along the minor axis. This directionally dependent difference in noise statistics was commonly referenced as "structured noise" which may evidence itself in streaks that propagate along the thick or major axis direction. If the radiation attenuation along the major axis became sufficiently great, the detector response due to the incident radiation could become almost the same as the detector noise, a condition known as "photon starvation". Photon starvation resulted in streaks that are very pronounced.

Increasing the amount of radiation produced by the x-ray tube reduced photon starvation, but had adverse effects along the minor axis. Specifically, if too much radiation were received by the radiation detectors, the detectors saturated.

One technique used in the past to control does and detector saturation was shaped compensators. That is, because the radiation path through the patient along the center of the fan was generally longer than along oblique angles of the fan, a compensator was provided for reducing the amount of radiation in the edges of the fan relative to the center. This fan angle dependent dose reduction enabled more radiation to pass along the longer, central paths without saturating the detectors with the radiation that passed along the central paths.

An x-ray tube is confined to deliver a predefined amount of radiation during any given time period. This restriction in the amount of radiation both limits the x-ray dose to the patient and prevents damage to the x-ray tube. If the x-ray tube were driven to produce too many x-rays, the anode may be damaged. If the surface temperature reached a sufficiently high level, the anode could warp or even melt, changing the surface characteristics of the anode. To protect the expensive x-ray tubes, most CT scanners operate at a given tube voltage, at one of several selectable tube currents, and only for a limited amount of time.

For these reasons, the CT gantry and the x-ray tube are commonly designed to have a constant angular velocity and a constant radiation profile.

In accordance with the present invention, a new and improved CT scanner and scanning method are provided which overcomes the above-referenced problems and others.

SUMMARY OF THE INVENTION

In accordance with the present invention, a CT scanning technique is provided in which the x-ray energy fluence rate provided to the subject is varied such that a generally constant x-ray energy fluence is received by each detector.

More specific to the present invention, angularly dependent radiation absorptive characteristics of the subject are determined. Based on this determination, the x-ray energy fluence directed toward the patient is adjusted in accordance with the relative angular position of the x-ray source and the subject.

In accordance with a more limited aspect of the present invention, one or both of the x-ray tube rotation speed and the x-ray output of the tube (e.g. tube mA) are varied in accordance with the relative angular position between the subject and the x-ray source.

One advantage of the present invention is that the resultant image has uniform noise texture. The reconstructed images have uniform noise statistics and appearances along all axes.

Another advantage of the present invention is that the average x-ray fluence delivered to all detectors is within the same preselected range. The x-ray energy fluence absorbed by the detectors across the thin portions of the subject are not in a different range than the x-ray energy fluence absorbed by detectors across a thick portion of the subject.

Another advantage of the present invention is that it can allow the radiation detectors to operate over a wider dynamic range. Varying the tube mA allows all detectors to operate at a large dosage end of the dynamic range without saturating.

Still further advantages of the present invention will become apparent to those of ordinary skill in the art upon reading and understanding the following detailed description.

BRIEF DESCRIPTION OF THE DRAWINGS

The invention may take form in various parts and arrangements of parts, and in various steps and arrangements of steps. The drawings are only for purposes of illustrating a preferred embodiment and are not to be construed as limiting the invention.

The FIGURE is a diagrammatic illustration of a CT scanner and control circuitry in accordance with the present invention.

DETAILED DESCRIPTION OF THE PREFERRED EMBODIMENT

A mechanical gantry portion 10 includes a stationary gantry portion 12 and a rotating gantry portion 14. The stationary gantry portion includes a stationary cylinder 16 in which a subject to be imaged is received. The rotatable gantry portion 14 is mounted on the stationary cylinder 16 by suitable bearings (not shown) to allow free rotational movement therearound. A motor 18 selectively rotates the rotatable gantry portion 14 around the cylinder 16. The motor may be a separate motor as shown in FIG. 1 connected by a chain or other suitable drive. Alternately, the cylinder 16 may be an integral portion of the "rotor" with the "stator" windings mounted to the rotatable gantry 14.

An x-ray tube 20 is mounted to the rotatable gantry portion 14 to rotate therewith. Appropriate slip ring electrical connections (not shown) are mounted between the cylinder 16 and the rotatable gantry portion 14 to provide electrical operating power to the x-ray tube 20. More specifically, a tube voltage (kV) is provided to bias the anode and cathode and a filament current is provided to adjust the tube current (mA) between the cathode and the anode. At a higher tube current, the x-ray beam generated by the interaction of the tube current and the anode has a higher x-ray energy fluence. The x-ray tube has an outlet port 22 through which radiation is directed toward the cylinder 16. A collimator and shutter arrangement 24 shapes the emitted radiation into a thin, fan-shaped beam which spans a scan circle, i.e. a circular imaging region 26 within the cylinder 16. A shutter selectively gates the radiation beam on and off. Radiation from the fan beam which has traversed the scan circle 26 impinges upon an array of radiation detectors 28. In the preferred embodiment, the radiation detectors 28 are arranged in a complete circle on the stationary gantry portion. Alternately, an arc of radiation detectors can be mounted to the rotating gantry portion to rotate with the radiation source.

An angular position monitoring means or resolver 30 monitors the angular position of the x-ray source 20 relative to a subject disposed in the scan circle 26. The angular position resolver 30 produces an indication of the current angular position of the x-ray source relative to the cylinder 16, hence the subject.

Each of the detectors 28 is connected With a sampling means 40 which samples a group of the detectors 28 which are receiving incident radiation. Each time the x-ray source rotates a preselected angular increment relative to the subject, the sampled group of detectors is incremented around the circle. In this manner, electronic data is collected which represents radiation attenuation along a preselected multiplicity of paths through the subject. A reconstruction means 42 reconstructs the radiation attenuation data using a filtered backprojection or other conventional algorithm into n image representation which is stored in an image memory 44 for display on a video monitor 46.

A digital motor speed controller 50 controls the motor 18 in order to control the angular velocity of the rotating gantry portion 14 relative to the stationary cylinder 16. A velocity versus angular position means 52, such as a look-up table, provides rotational speed information to the digital motor controller. More specifically to the preferred embodiment, the angular position resolver 30 addresses the angular position versus motor speed look-up table 52 with the current angular position to retrieve a corresponding motor speed designation which is communicated to the digital motor control 50. Each time the angular position resolver 30 senses a preselected increment f angular rotation, such as the angle spanned by one of detectors 28, the angular position resolver 30 indexes the address to the angular position versus speed look-up table 52 to provide the digital motor control 50 with an updated angular velocity. Of course, other means may be provided for converting angular position indications into speed control signals.

The angular position versus velocity look-up table may be programmed various ways. For example, the height and width dimensions of the region of interest of the patient can be measured and compared with a plurality of preselected height to width dimensions. A preprogrammed look-up table corresponding to the most similar height and width dimensions is loaded into the look-up table memory 52 to control rotational speed during the upcoming scan. This table can be derived through manual calculations, trial and error, or the like.

In the preferred embodiment, the angular position versus angular velocity look-up table 52 is derived empirically for each patient. An x-ray energy fluence measuring means 60 determines the average x-ray energy fluence which is being received by the arc of radiation detectors irradiated by the fan beam at each angular position of the x-ray tube 20 during a prediagnostic imaging scan. An x-ray energy fluence rate versus angular position table 62 correlates the measured x-ray energy fluence with angular position around the subject. An x-ray energy fluence rate reference means 64, such as a computer memory, stores one or more preselected reference x-ray energy or fluence rate at which the detectors 28 operate optimally. Preferably, the look up table includes a first reference x-ray energy fluence for diagnostic scanning and a second, lower reference x-ray energy fluence for screening. Optionally, additional higher and lower reference levels may be provided for other scanning procedures. A difference means 66 subtracts the x-ray energy fluence rate measured at each angle from the reference x-ray energy fluence rate to determine an x-ray energy fluence error or deviation for each angular position of the x-ray tube. An x-ray energy fluence error versus angular position memory means 68 correlates the x-ray energy fluence error or deviation corresponding to each angular position of the x-ray tube.

An x-ray energy fluence correcting means 70 calculates a speed or speed change which is projected to eliminate the x-ray energy fluence deviation. For example, the x-ray energy fluence correction means 70 may determine the percentage by which the x-ray energy fluence deviation or error differs from the standard reference x-ray energy fluence and increase or decrease the selected rotation speed by the same percentage. Optionally, the x-ray energy fluence correction means may take other variables into account. Optionally, a maximum x-ray energy fluence detecting means 72 detects the maximum x-ray energy fluence detected by any detector at each angular position and stores it in a maximum x-ray energy fluence versus angular position look-up table 74. The correction means 70 then determines the effect which the determined speed correction should have on each maximum x-ray energy fluence. For example, if the x-ray energy fluence deviation is 5% of the reference x-ray energy fluence, slowing the rotational speed by 5% can be expected to increase both the maximum and the average x-ray energy fluence by 5%. The maximum speed change allowed may be limited by the percentage difference between the maximum x-ray energy fluence for each angular position and the reference.

As another alternative, the technique discussed above may be used on the fly during a diagnostic scan to adjust speed, monitor for malfunctions, and the like. The average x-ray energy fluence means 60 can determine the currently measured x-ray energy fluence and use it to adjust the motor speed. This procedure is always one angular increment behind. When the motor speed corrections are calculated on the fly, a complete look-up table is not necessary. Rather, the speed indicating means 52 may be a counter, or the like, which is indexed up or down by the appropriate percentage to indicate the now desired motor speed to the digital motor control means 50. A rate of angular velocity change limiting means, such as an integrating or averaging circuit in the speed indicating means, may be used to assure that the gantry changes angular velocity smoothly without jerky movements.

Of course, the x-ray energy fluence impinging on the subject at each angular position of the x-ray tube can be adjusted in ways other than changing the speed at which the x-ray tube rotates. For example, the x-ray energy fluence produced by the x-ray tube may be varied in accordance with the angular position. To this end, a tube current means 80 identifies a selected tube current for each angular position. This may again be a look-up table analogous to table 52 for which the tube currents or current variations are calculated as described above.

An x-ray tube control circuit 82 controls the operating parameters of the x-ray tube 20. More specifically, the x-ray tube operating circuit includes a control circuit for controlling the tube current (mA). The x-ray tube control circuit 82 also controls the tube voltage applied between a filament or cathode 90 and an anode or target 92. Electrons boiled off from the heated filament are propelled by the tube voltage to travel from the filament to the anode to create the tube current, commonly measured in milliamps (mA). Preferably, the tube current is controlled by the bias on a grid disposed between the cathode and the anode. Optionally, the tube current can be adjusted by adjusting the current supplied to an x-ray tube filament to control its heating.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A CT scanner comprising:
   an examination region for receiving a subject that attenuates penetrating radiation more along some of a multiplicity of traversing paths than others;
   a source of penetrating radiation which directs a beam of radiation through the examination region;
   a motor means for rotating the radiation source through a multiplicity of angular positions around the examination region to pass the radiation through the subject along the multiplicity of traversing paths;
   a means for varying the energy fluence of radiation impinging upon the subject in accordance with the angular position of the radiation source such that an average energy fluence that traverses the subject is generally constant for all angular positions of the x-ray source;
   a radiation detection means for detecting the radiation with substantially the average energy fluence that has traversed the subject;
   a means for reconstructing image representations from the radiation detected by the detectors.

2. The scanner as set forth in claim 1 wherein the means for varying the x-ray energy fluence of radiation impinging on the subject includes a means for adjusting an x-ray energy fluence output of the radiation source as a function of angular position of the radiation source.

3. The scanner as set forth in claim 1 wherein the radiation source includes an x-ray tube in which x-rays are generated by a tube current flowing from a cathode to an anode and wherein the means for varying the x-ray energy fluence includes a means for varying the tube current.

4. A CT scanner comprising:
   an examination region for receiving a subject;
   a source of penetrating radiation which directs a beam of radiation through the examination region;
   a motor means for rotating the radiation source around the examination region, such that average radiation attenuation by the subject varies with an angular position of the radiation source therearound;

a means for varying the x-ray energy fluence of radiation impinging upon the subject in accordance with the angular position of the radiation source such that an average x-ray energy fluence that has traversed the subject is generally constant for all angular positions of the x-ray source, the means for varying the x-ray energy fluence impinging on the subject including:

a motor speed control means for selectively controlling the motor means to rotate the radiation source at selected angular velocities; and a speed designating means for designating angular velocities to the motor speed control means in accordance with the angular position of the radiation source;

a radiation detection means for detecting the radiation that has traversed the subject;

a means for reconstructing image representations from the radiation detected by the detectors.

5. The scanner as set forth in claim 4 further including an angular position resolving means for determining a current angular position of the radiation source relative to the subject, the angular position resolving means being operatively connected with the speed designating means.

6. The scanner as set forth in claim 4 wherein the speed designating means includes a look-up table.

7. The scanner as set forth in claim 6 further including a means for calculating look-up table values, the look-up table value calculating means including:

a means for determining an average x-ray energy fluence detected by the radiation detection means for each of a plurality of the angular positions of the radiation source;

a means for determining a variation in the x-ray energy fluence at each angular position; and, a means for determining an angular velocity speed correction for making the average x-ray energy fluence substantially constant at each angular position, corrected angular velocities being stored in the look-up table in conjunction with the corresponding angular positions.

8. A CT scanner comprising:

an examination region for receiving a subject;

an x-ray tube in which x-rays are generated by a tube current flowing from a cathode to an anode;

a motor means for rotating the radiation source around the examination region, such that average radiation attenuation by the subject varies with an angular position of the radiation source therearound;

a means for varying the x-ray energy fluence of radiation impinging upon the subject in accordance with the angular position of the radiation source such that an average x-ray energy fluence that has traversed the subject is generally constant for all angular positions of the x-ray source, the means for varying the x-ray energy fluence including a means for adjusting a bias on a grid between the cathode and the anode to vary the tube current;

a radiation detection means for detecting the radiation that has traversed the subject;

a means for reconstructing image representations from the radiation detected by the detectors.

9. A CT scanner comprising:

an examination region for receiving a non-cylindrical subject;

an x-ray tube in which x-rays are generated by a tube current from a cathode striking a target;

a motor means for rotating the radiation source around the examination region, such that average radiation attenuation by the subject varies with an angular position of the radiation source therearound;

an angular position resolving means for determining a current angular position of the x-ray tube relative to the subject;

an x-ray tube current varying means connected with the angular position resolving means for varying the x-ray tube current such that the x-ray energy fluence of radiation impinging upon the subject in accordance with the angular position of the radiation source such that an average x-ray energy fluence that has traversed the subject is generally constant for all angular positions of the x-ray source;

a radiation detection means for detecting the radiation that has traversed the subject;

a means for reconstructing image representations from the radiation detected by the detectors.

10. The scanner as set forth in claim 9 wherein the tube current varying means includes a look-up table means which correlates angular position and radiation variations.

11. The scanner as set forth in claim 10 further including a means for calculating look-table values, the look-up table value calculating means including:

a means for determining a variation in an average of the x-ray fluence detected at a plurality of the angular positions; and, a means for determining tube current corrections for making the average x-ray energy fluence substantially constant, the tube current corrections being stored in the look-up table in conjunction with the corresponding angular positions.

12. A radiation examination means comprising:

a source of penetrating radiation which rotates relative to a subject that has different radiation attenuation properties at different angular directions therethrough;

a means for detecting radiation generated by the radiation source which has been transmitted through the subject;

a means for determining a current angular position of the radiation source relative to the subject;

a means for adjusting an energy fluence of the radiation which impinges upon the subject between each sampling of the radiation detection means in accordance with the current relative angular position of the radiation source and the radiation attenuation properties of the subject along the angular direction from the current radiation source position through the subject such that an average energy fluence of radiation that traverses the subject is held substantially constant for all angular positions of the radiation source.

13. The system as set forth in claim 12 further including an image reconstruction means connected with the radiation detecting means for reconstructing an image representation from the detected radiation.

14. A CT scanner comprising:

a source of a fan-shaped swath of radiation;

a means for rotating the fan-shaped swath of radiation relative to a subject whose radiation absorbency varies with a relative angular position between the fan-shaped swath and the subject a radiation detection means for detecting the radiation which has traversed the subject;

a means for selectively adjusting at least one of an amount of radiation impinging upon the subject and a rotation speed of the radiation swath in accordance with the sampled radiation and the relative angular position between the swath and the subject to adjust for the varying radiation absorbency of the subject with angular position between the fan-shaped swath and the subject such that an average energy fluence of the radiation which has traversed the subject and is detected by the detectors remains constant.

15. A method of generating an image representation of a subject of non-uniform cross-section, the method comprising:

generating a swath of radiation which is directed to pass through the subject;

rotating the fan-shaped swath relative to the subject such that the fan-shaped swath passes through the subject from a plurality of angular orientations;

repeatedly sampling the radiation which has passed through the patient at different relative angles;

selectively adjusting at least one of an amount of radiation impinging upon the subject and a rotation speed of the radiation swath in accordance with the sampled radiation and the relative angular position between the swath and the subject.

16. The method as set forth in claim 15 wherein the adjusting step includes adjusting a rotational speed of the swath of radiation relative to the patient such that an average x-ray energy fluence of the radiation sampled across the swath at each relative angular position is substantially constant.

17. The method as set forth in claim 16 wherein the radiation which has passed through the subject is sampled at constant intervals.

18. The method as set forth in claim 16 further including determining a selected angular velocity for each angular position including:

rotating the swath of radiation with a constant x-ray energy fluence around the subject at a constant angular velocity;

determining an average x-ray energy fluence of radiation sampled across the swath at each of a plurality of angular positions;

determining a deviation in the average sampled x-ray energy fluence at the angular positions;

determining a selected angular velocity for each angular position to hold the average sampled x-ray energy fluence substantially constant at the angular positions.

19. The method as set forth in claim 15 wherein the step of generating the swath of radiation includes directing a tube current from a cathode to an anode of an x-ray tube, interaction of the tube current and the anode generating the radiation and wherein the adjusting step includes adjusting the tube current in accordance with angular position.

20. The method as set forth in claim 19 wherein the step of adjusting the tube current includes adjusting a bias on a grid between the cathode and the anode.

* * * * *